Figure 1:
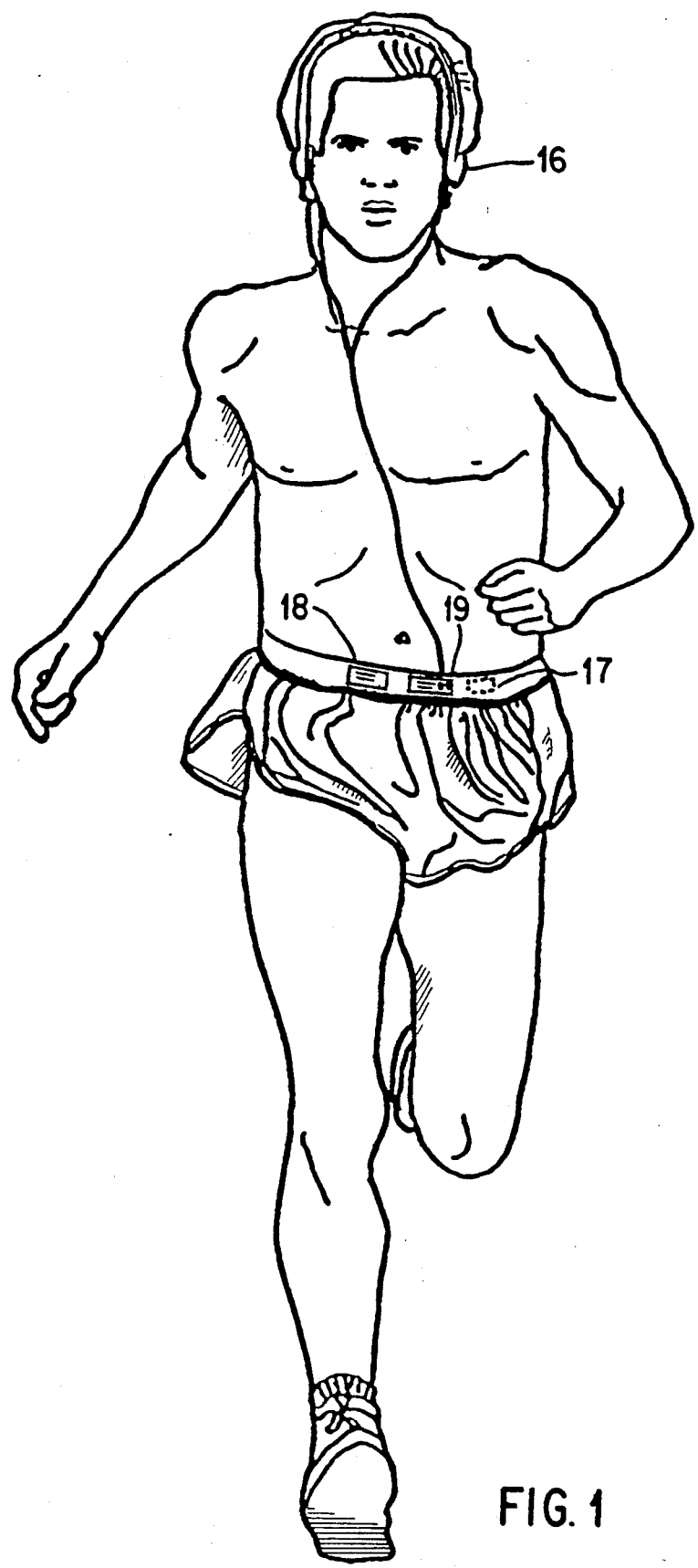

United States Patent [19]
Dotan

[11] Patent Number: 5,314,389
[45] Date of Patent: May 24, 1994

[54] EXERCISE MONITOR

[76] Inventor: Simon Dotan, 47 Vradim Street, Natanya, Israel

[21] Appl. No.: 851,684

[22] Filed: Mar. 12, 1992

[30] Foreign Application Priority Data

Mar. 12, 1991 [IL] Israel .................................. 097526

[51] Int. Cl.$^5$ .............................................. A61B 5/00
[52] U.S. Cl. .......................................... 482/3; 482/8; 482/900; 482/901
[58] Field of Search ....................... 482/3, 8, 900–903, 482/5; 128/644, 668, 689, 362; 607/1

[56] References Cited

U.S. PATENT DOCUMENTS

| | | | |
|---|---|---|---|
| 4,674,743 | 6/1987 | Hirano | 482/8 |
| 4,867,442 | 9/1989 | Matthews | 482/901 X |
| 4,911,427 | 3/1990 | Matsumoto et al. | 482/3 X |
| 5,076,281 | 12/1991 | Gauish | 128/721 |

Primary Examiner—Richard J. Apley
Assistant Examiner—Glenn E. Richman
Attorney, Agent, or Firm—Keck, Mahin & Cate

[57] ABSTRACT

A device which provides an exercising person information at any desired period of time about his pulse rate at that instant. The information is given as vocal information, and the device comprises an ECG unit with electrodes adapted to be attached to the human body, one of which forms part of an earphone, filter and amplification means, a speech synthesizer, and means for evaluating instantly the ECG and for giving a vocal indication of the instant pulse rate. The device is of special value for the monitoring of the pulse rate during jogging and similar types of exercise, the information being provided vocally. A preferred embodiment comprises a wireless set and/or tape recorder, with means for dimming the output of such radio or tape while a pulse rate is announced at predetermined intervals.

9 Claims, 4 Drawing Sheets

EXERCISE MONITOR

FIELD OF INVENTION

The invention relates to a device comprising in combination an ECG instrument and a radio or tape or any other auxiliary vocal instrument, electrode means adapted to be attached to the human body, due to the fact that the instrument is an integrated system of two electronic devices, and a battery compartment and these are arranged on a chest belt, it is possible to locate on the back side of the belt the receiving electrodes for the ECG signal. On the other hand, taking the advantage of this device that has to use earphones, one of the electrodes can be part of an earphone, while the other one is located on the back of the chest belt. All these are connected to electronic means for evaluating the ECG and for providing a vocal indication of the heart rate, while listening to radio or auxiliary audio means, the overall control being by a microprocessor.

The instrument is a portable one, to be worn by a person engaged in exercise such as jogging, walking, cycling, rowing, climbing or other physical activity where the monitoring of the heart rate is of importance.

BACKGROUND OF THE INVENTION

Physical exercise is related to the pulse rate of the exercising person. In many cases the severity of the effort ought to be adjusted to the pulse rate, which is indicative of the physical effort. There exists portable monitors like respirometers, ECG instruments and the like, and some of these can be worn by an exercising person. The problem is the read-out of the pulse or respiratory rate at any given instant, as certain persons ought not to exceed a certain pulse rate, so as not to over-excert the heart. Devices with a digital presentation of pulse rate are known.

The system of the present invention is in the form of a convenient portable form, easily worn by an exercising person and especially during walking, jogging, etc. While exercising the user can listen to his favorite radio station, cassette, etc. The vocal indications of pulse rate are at predetermined intervals, controlled by the microprocessor and thus preventing "over-exercising", and furthermore one of the earphones serves as electrode, which is an advantage in that it uses the earphone for dual purposes: as earphones and at the same time as electrode, providing strong signals to the ECG device.

SUMMARY OF THE INVENTION

The invention relates to a portable device, to be worn by an exercising person, and which is adapted to provide at any desired instant or periodically, information on the heart rate (pulse) at the given instant. The vocal indication of the information is very convenient for the exercising person and does not destract from the actual exercise.

The device of the invention comprises of a combination of a radio or tape or other audio auxiliary instrument attached to an ECG instrument, provided with electrodes which can be attached to the body of the monitored person, where the earphone serves as one of the electrodes, means for evaluating the resulting ECG at any given instant, and to translate it to a vocal message to the exercising person, thus enabling such person to adjust the rate of exercise to his pulse rate at any desired moment.

The instrument includes means for translating the ECG electronically to a digital indication for the instantaneous pulse rate, and which is transduced to a vocal output informing the exercising person by such vocal indication about his pulse.

The system advantageously combines a Radio or Tape or any other audio auxiliary instrument, which may be worn on the same belt. Advantageously the electrodes are such that one is positioned at the backside of the belt at chest height, and the other one is part of one of the earphones or the two electrodes are located at the back of the chest belt.

Figure 2:
Figure 3:
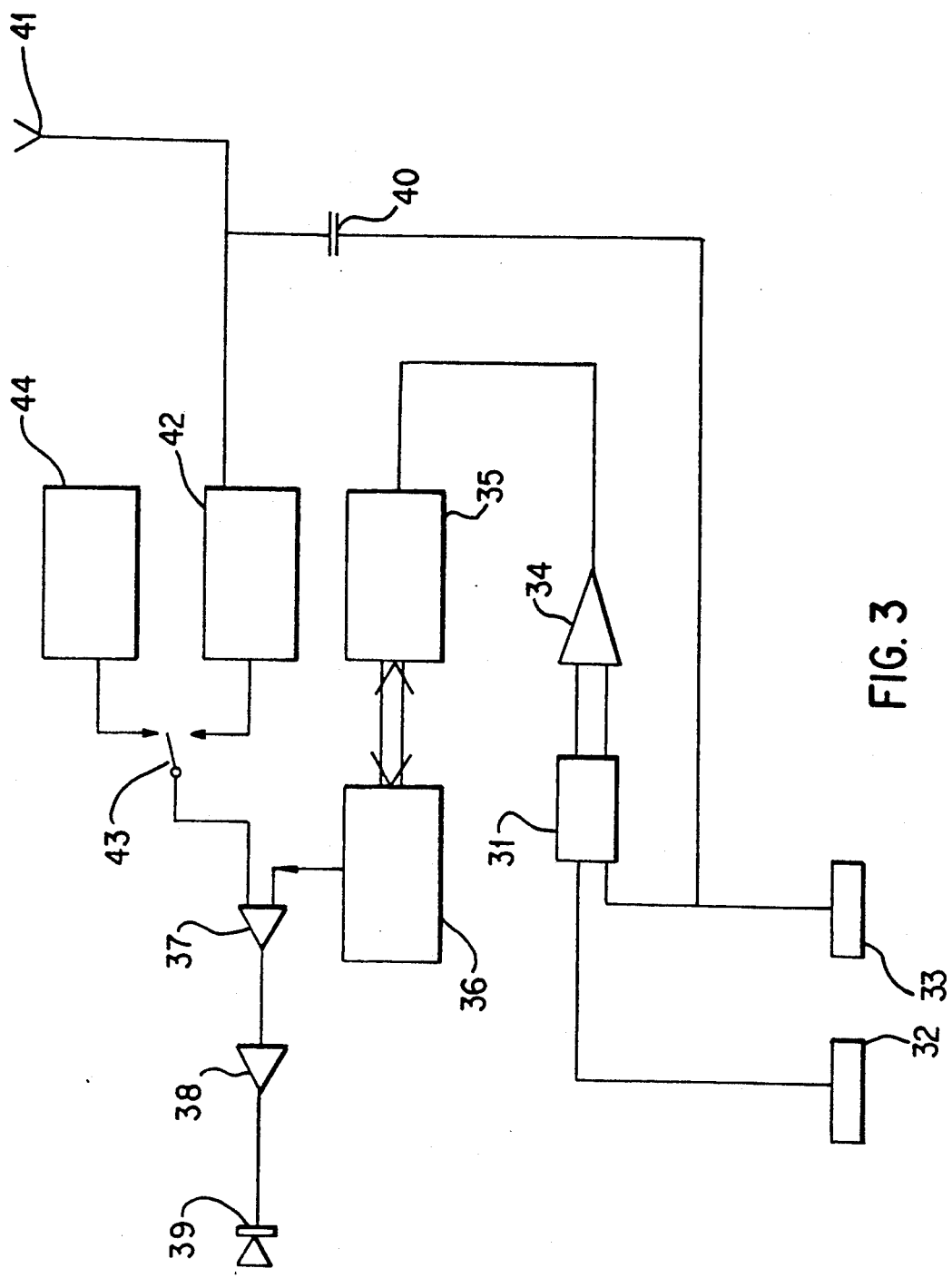
Figure 4:
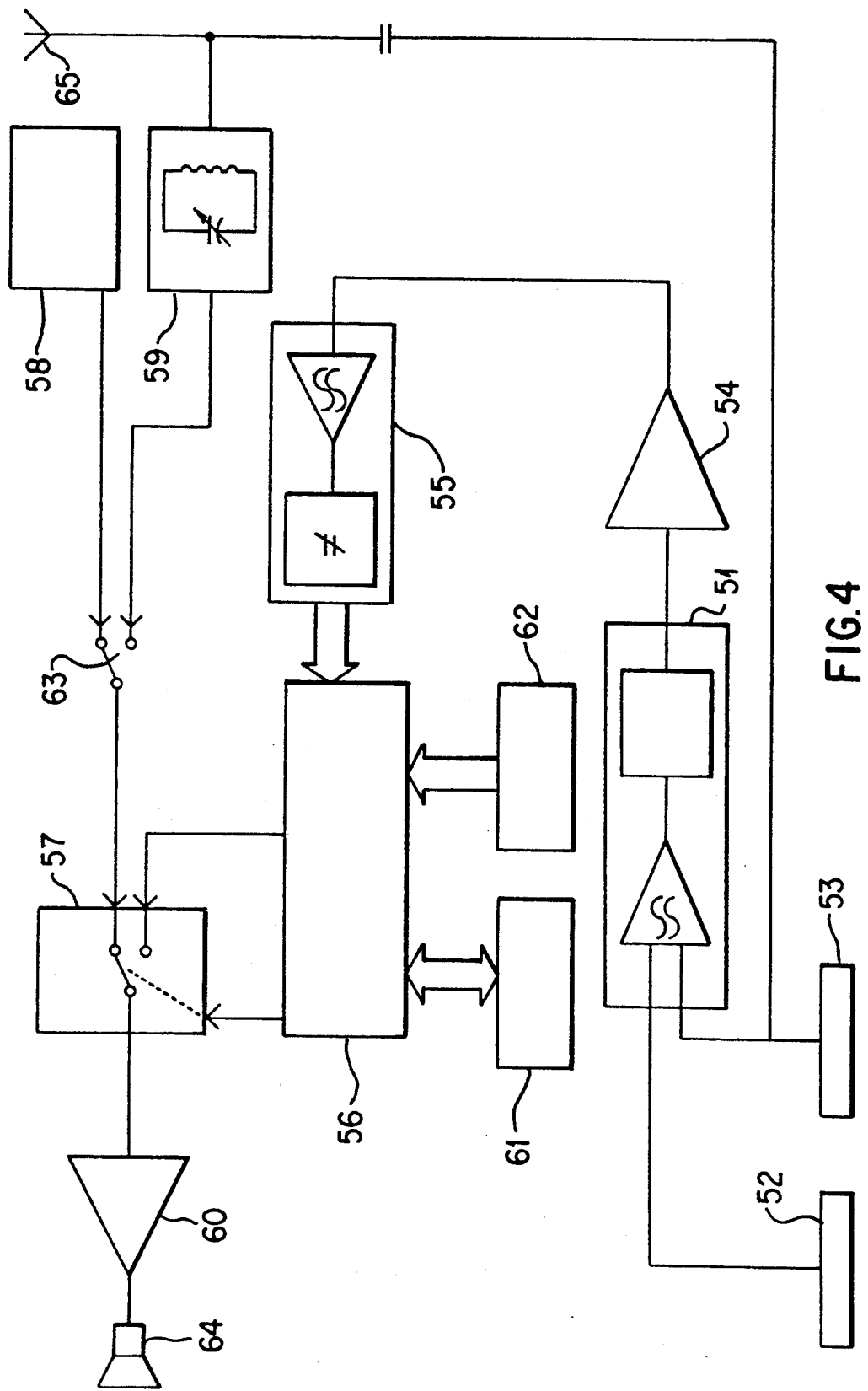

The device of the invention can be provided in various forms and configurations. The enclosed schematical Figures demonstrate the invention, and are illustrative only. In the enclosed figures, FIG. 1 is a front view of a jogger wearing a system of the invention. In the configuration one electrode is located at the earphone while the other one is at the back of the belt which in this case is a waist belt, FIG. 2 is a modification of the system of FIG. 1. In this configuration the device is located on the chest and in this case, there are two possibilities for the ECG pickup—1) same as in FIG. 1 I.E., one electrode in the earphone and one on the back of the belt, 2) both electrodes located on the back of the belt, FIG. 3 is a block diagram of a system of the invention, FIG. 4 is an electronic schematic describing the principles of the system.

As shown in FIG. 1, the system comprises of an ECG apparatus 19, provided with electrode means 17/16 at the waist level and as part of the earphone 16; a radio/-tape 18, provided with a power source (battery or rechargable batteries), a receiver 19 of the ECG signal containing control means, earphones 16 which are used to convey the vocal message to the jogger and as the second electrode.

A modification of the system of FIG. 1 is illustrated in FIG. 2, where the jogger wears around his chest a belt supporting the ECG unit and one electrode 14, and also the radio/tape and transducer means 15, such belt 11 extending around the shoulders and provided with connecting means 12 to the earphones 13, which house the second electrode which forms part of the ECG circuit. There is provided an electronic circuit for translating the ECG curve to a digital signal of the pulse rate, which is converted to a vocal indication (via the earphones) of such pulse rate.

The system of the invention illustrated with reference to FIG. 3, comprises in combination an ECG 31 provided with filter means, electrodes attachable to the body, 32 and 33 extending from 31, the output of the ECG 31 is passed via amplifier 34 to special filter 35 which are translating the ECG signal into digital 35 which is connected to a microcontroller and speech synthesizer 36, connected to active combiner 37 which is controlled by the microcontroller 36 via audio amplifier 38 to earphones 39, said one electrode 33 being connected via capacitor 40 on the one hand to antenna 41, and via radio 42 to said active combiner 37, there being provided a switch 43 for the selection of audio means which is a connection means of tape or any audio auxiliary means 44 to said active combiner 37. The components are conventional ones, and their choice is within the capability of one skilled in the art.

FIG. 4 is the electronic schematics describing the basis of FIG. 3, where ECG signal filter 55 that enables microprocessor 56 to count rate of beats is connected to the controllor that controls the mode of operation, which controls the active semiconductor switch controlled by the microcontrollor 57, and as another option of the user any other audio auxiliary means 58 or a built-in tuneable radio 59. These options are controlled by the user switch 63. Where voice synthesizer 61 in conjunction to the controllor ROM memory 62 and voice generator announcement 61 are controlled by control microprocessor 56 providing an input of a vocal announcement via switch 57.

I claim:

1. A portable exercise system providing vocal instantaneous indications of a pulse rate to an exercising person, comprising an ECG unit including electrode means, means for amplifying the output of the ECG unit and means for converting the amplified output to a vocal indication of the pulse rate, the means for converting including earphones, said earphones being adapted for connection to an audio player means for playing audio information via the earphones, wherein one of the electrode means also forms part of the earphones, said system further comprising an integrated microcontroller adapted to reduce the volume of the audio information at predetermined intervals and output said vocal indication of the pulse rate.

2. An exercise system for providing a vocal indication of a pulse rate at any desired point of time to an exercising person, comprising in combination an ECG device including electrodes for attachment to the person, earphones, one of the electrodes forming part of one of the earphones, a control means for controlling input to the earphones, a filter and amplification means connected between the ECG device and the control means, the control means comprising a speech synthesizer and being connected to an active combiner, where the combiner is adapted for connection to an audio player means for playing audio information via the earphones, the control means being operable to control the combiner, said combiner being connected via an audio amplifier to the earphones.

3. A system according to claim 1, where the microcontroller is operable to reduce the volume of the audio information for the period of time during which the vocal indication of the pulse rate is being made.

4. A system according to claim 1, where the electrode means comprise a conductive polymeric material.

5. A system according to claim 1, where the ECG unit and the audio player means are attached to a belt adapted to be worn around the torso of the person, where the electrode means are an integral part of the rear of such belt, and are adapted to be in contact with the skin of the user.

6. An exercise system according to claim 1, where the audio player means comprises one of the group consisting of a radio, a tape player and an audio auxiliary means.

7. An exercise system according to claim 2, where the audio player means comprises one of the group consisting of a radio, a tape player and an audio auxiliary means.

8. A portable exercise system adapted to be worn by an exercising person wearing a belt, the system comprising earphones, an ECG unit having two electrodes, one of which is adapted to contact the torso of the exercising person, the other electrode forming part of one of the earphones, an amplifier for amplifying the output of the ECG unit and a speech synthesizer connected to the amplifier for converting the resulting amplified output to a vocal indication of the pulse rate of the exercising person, a microcontroller connected to said speech synthesizer, an audio player means for playing music via the earphones and also being connected to said microcontroller, said microcontroller being operable to dim the output of the music during predetermined periods of time and couple the output of said speech synthesizer to the earphone so that the pulse rate is vocally indicated via said earphones.

9. An exercise system according to claim 7, where the microcontroller is operable to dim the output of music when a predetermined pulse rate is reached and connect the output of said speech synthesizer so that the pulse rate is vocally indicated via said earphones.

* * * * *